(12) United States Patent
Meskens et al.

(10) Patent No.: US 9,936,312 B2
(45) Date of Patent: *Apr. 3, 2018

(54) ACOUSTIC OUTPUT DEVICE WITH ANTENNA

(71) Applicant: GN HEARING A/S, Ballerup (DK)

(72) Inventors: Werner Meskens, Opwiji (BE); Tadeusz Jurkiewicz, Rozelle (AU); Steve Winnall, Stanmore (AU); Limin Zhong, Denistone (AU)

(73) Assignee: GN HEARING A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/455,081

(22) Filed: Mar. 9, 2017

(65) Prior Publication Data
US 2017/0180885 A1 Jun. 22, 2017

Related U.S. Application Data

(63) Continuation of application No. 15/188,780, filed on Jun. 21, 2016, which is a continuation of application (Continued)

(51) Int. Cl.
*H04R 25/00* (2006.01)

(52) U.S. Cl.
CPC .......... *H04R 25/554* (2013.01); *H04R 25/60* (2013.01); *H04R 2225/021* (2013.01);
(Continued)

(58) Field of Classification Search
CPC ..... A61N 1/36032; H04R 25/556; H04R 3/08
See application file for complete search history.

(56) References Cited

U.S. PATENT DOCUMENTS 2,535,063 A 12/1950 Halstead
2,573,438 A 10/1951 Hathaway et al.
(Continued)

FOREIGN PATENT DOCUMENTS

CN 1684549 A 10/2005
CN 101835082 A 9/2010
(Continued)

OTHER PUBLICATIONS

Notice of Allowance and Fee(s) due dated Apr. 11, 2017 for related U.S. Appl. No. 13/271,180.
(Continued)

*Primary Examiner* — Michael Carey
*Assistant Examiner* — Natasha Patel
(74) *Attorney, Agent, or Firm* — Vista IP Law Group, LLP

(57) ABSTRACT

A hearing aid includes: a hearing aid component configured to be arranged at a head of a user, and away from an ear canal of the user, the hearing aid component configured to provide a signal to an earpiece; the earpiece configured to be arranged at the ear of the user, and configured to provide an acoustic output to the user; and a coupling element configured for coupling the hearing aid component and the earpiece, the coupling element having a tube and an electrically conducting element; wherein the electrically conducting element in the coupling element of the hearing aid is configured to operate as a part of an antenna for wireless communication, and wherein the electrically conducting element is configured for electromagnetic signal emission and/or electromagnetic signal reception.

19 Claims, 10 Drawing Sheets

Related U.S. Application Data

No. 14/199,263, filed on Mar. 6, 2014, now Pat. No. 9,446,233, which is a continuation of application No. 12/131,867, filed on Jun. 2, 2008, now Pat. No. 8,934,984.

(60) Provisional application No. 60/924,807, filed on May 31, 2007, provisional application No. 60/924,800, filed on May 31, 2007.

(52) U.S. Cl.
CPC .... *H04R 2225/025* (2013.01); *H04R 2225/51* (2013.01); *H04R 2225/55* (2013.01)

(56) References Cited

U.S. PATENT DOCUMENTS

| | | | |
|---|---|---|---|
| 3,276,028 A | | 9/1966 | Paul E Mayes et al. |
| 4,334,315 A | | 6/1982 | Ono et al. |
| 4,652,888 A | | 3/1987 | Deasy |
| 4,741,339 A | | 5/1988 | Harrison et al. |
| 4,924,237 A | | 5/1990 | Honda et al. |
| 5,426,719 A | * | 6/1995 | Franks ................ H04R 1/1083 381/72 |
| 5,621,422 A | | 4/1997 | Wang |
| 5,721,783 A | | 2/1998 | Anderson |
| 5,760,746 A | | 6/1998 | Kawahata |
| 5,761,319 A | | 6/1998 | Dar et al. |
| 6,161,036 A | | 12/2000 | Matsumura |
| 6,456,720 B1 | | 9/2002 | Brimnall |
| 6,515,629 B1 | | 2/2003 | Kuo et al. |
| 6,748,094 B1 | | 6/2004 | Tziviskos et al. |
| 6,766,201 B2 | | 7/2004 | Von Arx et al. |
| 6,911,944 B2 | | 6/2005 | Sekine |
| 6,924,773 B1 | | 8/2005 | Paratte |
| 7,002,521 B2 | | 2/2006 | Egawa et al. |
| 7,020,298 B1 | | 3/2006 | Tziviskos et al. |
| 7,027,608 B2 | | 4/2006 | Fretz et al. |
| 7,046,499 B1 | * | 5/2006 | Imani ................ H01G 4/35 174/152 GM |
| 7,154,442 B2 | | 12/2006 | Van Wonterghem et al. |
| 7,256,747 B2 | | 8/2007 | Victorian et al. |
| 7,446,708 B1 | | 11/2008 | Nguyen et al. |
| 7,450,078 B2 | | 11/2008 | Knudsen |
| 7,570,777 B1 | | 8/2009 | Taenzer et al. |
| 7,593,538 B2 | | 9/2009 | Polinske |
| 7,630,772 B1 | * | 12/2009 | Walsh ................ A61N 1/0541 607/55 |
| 7,652,628 B2 | | 1/2010 | Zweers |
| 7,652,678 B2 | | 1/2010 | Brunner |
| 7,791,551 B2 | | 9/2010 | Platz |
| 7,978,141 B2 | | 7/2011 | Chi et al. |
| 8,300,863 B2 | | 10/2012 | Knudsen et al. |
| 8,401,211 B2 | | 3/2013 | Angst |
| 8,494,197 B2 | | 7/2013 | Polinske et al. |
| 8,934,984 B2 | | 1/2015 | Meskens et al. |
| 9,446,233 B2 | | 9/2016 | Meskens et al. |
| 2002/0091337 A1 | * | 7/2002 | Adams ................ H04R 25/554 600/559 |
| 2003/0045283 A1 | | 3/2003 | Hagedoorn |
| 2003/0098812 A1 | | 5/2003 | Ying |
| 2004/0010181 A1 | | 1/2004 | Feeley et al. |
| 2004/0073275 A1 | | 4/2004 | Malian et al. |
| 2004/0080457 A1 | | 4/2004 | Guo et al. |
| 2004/0138723 A1 | | 7/2004 | Malick et al. |
| 2004/0246179 A1 | | 12/2004 | Chen et al. |
| 2005/0068234 A1 | | 3/2005 | Hung et al. |
| 2005/0094840 A1 | | 5/2005 | Harano |
| 2005/0099341 A1 | | 5/2005 | Zhang et al. |
| 2005/0244024 A1 | | 11/2005 | Fischer et al. |
| 2005/0245289 A1 | | 11/2005 | Yoshino |
| 2005/0248717 A1 | | 11/2005 | Howell et al. |
| 2005/0251225 A1 | | 11/2005 | Faltys et al. |
| 2006/0012524 A1 | | 1/2006 | Mierke et al. |
| 2006/0018496 A1 | | 1/2006 | Niederdrank et al. |
| 2006/0052144 A1 | | 3/2006 | Seil et al. |
| 2006/0056649 A1 | * | 3/2006 | Schumaier ........... H04R 25/606 381/326 |
| 2006/0061512 A1 | | 3/2006 | Asano et al. |
| 2006/0064037 A1 | * | 3/2006 | Shalon ................ A61B 5/0006 600/586 |
| 2006/0071869 A1 | | 4/2006 | Yoshino et al. |
| 2006/0115103 A1 | | 6/2006 | Feng et al. |
| 2006/0181466 A1 | | 8/2006 | Krupa |
| 2006/0192723 A1 | | 8/2006 | Harada et al. |
| 2007/0080889 A1 | | 4/2007 | Zhang |
| 2007/0171134 A1 | | 7/2007 | Yoshino et al. |
| 2007/0229369 A1 | | 10/2007 | Platz |
| 2007/0229376 A1 | | 10/2007 | Desclos et al. |
| 2007/0230714 A1 | | 10/2007 | Armstrong |
| 2007/0230727 A1 | | 10/2007 | Sanguino et al. |
| 2007/0285321 A1 | | 12/2007 | Chung et al. |
| 2008/0024375 A1 | | 1/2008 | Martin et al. |
| 2008/0056520 A1 | | 3/2008 | Christensen et al. |
| 2008/0079645 A1 | | 4/2008 | Higasa et al. |
| 2008/0231524 A1 | | 9/2008 | Zeiger et al. |
| 2008/0300658 A1 | | 12/2008 | Meskens |
| 2008/0304686 A1 | | 12/2008 | Meskens et al. |
| 2009/0069060 A1 | | 3/2009 | Kim |
| 2009/0074221 A1 | | 3/2009 | Westermann |
| 2009/0124201 A1 | | 5/2009 | Meskens |
| 2009/0169038 A1 | | 7/2009 | Knudsen et al. |
| 2009/0196444 A1 | | 8/2009 | Solum |
| 2009/0214064 A1 | | 8/2009 | Wu |
| 2009/0231204 A1 | | 9/2009 | Shaker et al. |
| 2009/0231211 A1 | | 9/2009 | Zweers |
| 2009/0243944 A1 | | 10/2009 | Jung et al. |
| 2009/0273530 A1 | | 11/2009 | Chi et al. |
| 2009/0315787 A1 | | 12/2009 | Schatzle |
| 2010/0020994 A1 | | 1/2010 | Christensen et al. |
| 2010/0033380 A1 | | 2/2010 | Pascolini et al. |
| 2010/0079287 A1 | | 4/2010 | Forster |
| 2010/0109953 A1 | | 5/2010 | Tang |
| 2010/0158291 A1 | | 6/2010 | Polinske et al. |
| 2010/0158293 A1 | | 6/2010 | Polinske et al. |
| 2010/0158295 A1 | | 6/2010 | Polinske et al. |
| 2010/0172525 A1 | | 7/2010 | Angst et al. |
| 2010/0245201 A1 | | 9/2010 | Hossain et al. |
| 2010/0321269 A1 | | 12/2010 | Ishibana et al. |
| 2011/0007927 A1 | | 1/2011 | Hedrick et al. |
| 2011/0022121 A1 | | 1/2011 | Meskins |
| 2011/0129094 A1 | | 6/2011 | Petersen |
| 2011/0249836 A1 | | 10/2011 | Solum |
| 2011/0285599 A1 | | 11/2011 | Smith |
| 2011/0294537 A1 | | 12/2011 | Vance |
| 2012/0087506 A1 | | 4/2012 | Ozden |
| 2012/0093324 A1 | | 4/2012 | Sinasi |
| 2012/0154222 A1 | | 6/2012 | Oh et al. |
| 2012/0326938 A1 | | 12/2012 | Grossman |
| 2013/0308805 A1 | | 11/2013 | Ozden |
| 2013/0342407 A1 | | 12/2013 | Kvist |
| 2014/0010392 A1 | | 1/2014 | Kvist |
| 2014/0097993 A1 | | 4/2014 | Hotta |
| 2014/0185848 A1 | | 7/2014 | Ozden et al. |
| 2014/0321685 A1 | | 10/2014 | Rabel |
| 2014/0378958 A1 | | 12/2014 | Leussler |

FOREIGN PATENT DOCUMENTS

| | | |
|---|---|---|
| CN | 102318138 A | 1/2012 |
| CN | 102570000 A | 7/2012 |
| DE | 3625891 A1 | 2/1988 |
| DE | 10 2004 017832 | 10/2005 |
| DE | 10 2008 022 127 A1 | 11/2009 |
| EP | 1 231 819 A2 | 8/2002 |
| EP | 1 294 049 A1 | 3/2003 |
| EP | 1 465 457 A2 | 10/2004 |
| EP | 1 465 457 A3 | 10/2004 |
| EP | 1 589 609 | 10/2005 |
| EP | 1 594 188 A1 | 11/2005 |
| EP | 1 681 903 A2 | 7/2006 |
| EP | 1 763 145 A1 | 3/2007 |
| EP | 1 939 984 A1 | 2/2008 |
| EP | 1 953 934 A1 | 8/2008 |

(56) References Cited

FOREIGN PATENT DOCUMENTS

| | | |
|---|---|---|
| EP | 2 088 804 A1 | 8/2009 |
| EP | 2 200 120 A2 | 6/2010 |
| EP | 2 200 120 A3 | 6/2010 |
| EP | 2 207 238 A1 | 7/2010 |
| EP | 2 229 009 A1 | 9/2010 |
| EP | 2 302 737 | 3/2011 |
| EP | 2 458 674 A2 | 5/2012 |
| EP | 2 637 251 | 11/2013 |
| EP | 2 680 366 | 1/2014 |
| EP | 2 723 101 A2 | 4/2014 |
| EP | 2 723 101 A3 | 4/2014 |
| EP | 2 765 650 | 8/2014 |
| JP | S59-97204 | 6/1984 |
| JP | H10-209739 | 8/1998 |
| JP | 2005-304038 A | 10/2005 |
| JP | 2006/025392 | 1/2006 |
| JP | 2006-033853 A | 2/2006 |
| JP | 2012-090266 | 5/2012 |
| WO | WO 98/44762 | 10/1998 |
| WO | WO 03/026342 | 3/2003 |
| WO | WO 03/107548 | 12/2003 |
| WO | WO 2004/110099 A2 | 12/2004 |
| WO | WO 2005/076407 A2 | 8/2005 |
| WO | WO 2005/081583 A1 | 9/2005 |
| WO | WO 2006/055884 A2 | 5/2006 |
| WO | WO 2006122836 A2 | 11/2006 |
| WO | WO 2007/045254 A1 | 4/2007 |
| WO | WO 2007/140403 A2 | 6/2007 |
| WO | WO 2008/012355 A1 | 1/2008 |
| WO | WO 2009/010724 A1 | 1/2009 |
| WO | WO 2009/098858 A1 | 8/2009 |
| WO | WO 2009117778 A1 | 10/2009 |
| WO | WO 2010/065356 A1 | 6/2010 |
| WO | WO 2011099226 | 8/2011 |
| WO | WO 2012059302 | 5/2012 |
| WO | WO 2014090420 A1 | 6/2014 |

OTHER PUBLICATIONS

Notification of First Office Action dated Jan. 26, 2017 for related Chinese Patent Application No. 201310713296.7, 21 pages.
1st Technical Examination and Search Report dated Jan. 24, 2013 for DK Patent Application No. PA 2012 70411, 5 pages.
1st Technical Examination and Search Report dated Jan. 25, 2013 for DK Patent Application No. PA 2012 70412, 4 pages.
Advisory Action dated Aug. 29, 2014 for U.S. Appl. No. 13/740,471.
Chinese Office Action and Search Report dated Dec. 4, 2013 for related CN Patent Application No. 201110317229.4.
Chinese Office Action and Search Report dated Nov. 12, 2013 for related CN Patent Application No. 201110317264.6.
Danish Office Action dated Apr. 30, 2012 for Danish Patent Application No. PA 2011 70566.
Danish Office Action dated May 1, 2012 for Danish Patent Application No. PA 2011 70567.
English Abstract of Foreign Reference DE 10 2008 022 127 A1 (included in 1st page of Foreign Document No. 3).
Extended European Search Report dated Apr. 17, 2014 for EP Patent Application No. 13192316.1.
Extended European Search Report dated Apr. 22, 2014 for EP Patent Application No. 13192323.7.
Extended European Search Report dated Mar. 7, 2014 for EP Patent Application No. 11184503.8.
Extended European Search Report dated Mar. 7, 2014 for EP Patent Application No. 11184507.9.
Extended European Search Report dated May 6, 2014 for EP Patent Application No. 13175258.6.
Final Office Action dated Aug. 29, 2014 for U.S. Appl. No. 13/848,605.
Final Office Action dated Feb. 27, 2014, for U.S. Appl. No. 13/271,180.
Final Office Action dated May 19, 2014 for U.S. Appl. No. 13/740,471.
First Danish Office Action dated Apr. 26, 2011 for Danish Patent Application No. PA 2010 00931.
First Office Action dated Feb. 12, 2013 for Japanese Patent Application No. 2011-224711.
First Technical Examination and Search Report dated Jan. 18, 2013 for DK Patent Application No. PA 2012 70410, 4 pages.
Fourth Danish Office Action, Intention to Grant dated Feb. 13, 2013 for Danish Patent Application No. PA 2010 00931.
Non-final Office Action dated Jan. 2, 2014 for U.S. Appl. No. 13/740,471.
Non-Final Office Action dated Jul. 29, 2014 for U.S. Appl. No. 13/917,448.
Non-Final Office Action dated Mar. 27, 2014 for U.S. Appl. No. 13/848,605.
Non-Final Office Action dated May 22, 2014 for U.S. Appl. No. 13/271,170.
Non-final Office Action dated Oct. 8, 2013 for U.S. Appl. No. 13/271,180.
Notice of Reasons for Rejection dated May 21, 2013 for Japanese Patent Application No. 2011-224705.
Second Danish Office Action dated Apr. 24, 2012 for Danish Patent Application No. PA 2010 00931.
Second Technical Examination—Intention to Grant dated Jul. 8, 2013 for DK Patent Application No. PA 2012 70412, 2 pages.
Second Technical Examination dated Aug. 6, 2013 for DK Patent Application No. PA 2012 70411, 2 pages.
Second Technical Examination dated Jul. 12, 2013, for DK Patent Application No. PA 2012 70410, 2 pages.
Third Danish Office Action dated Oct. 17, 2012 for Danish Patent Application No. PA 2010 00931.
Third Technical Examination dated Jan. 31, 2014, for DK Patent Application No. PA 2012 70410, 2 pages.
Office Action dated Jun. 17, 2014 in Japanese Patent Application No. 2013-258396, 3 pages.
First Technical Examination dated Jun. 25, 2014 for DK Patent Application No. PA 2013 70665, 5 pages.
First Technical Examination dated Jun. 26, 2014 for DK Patent Application No. PA 2013 70664, 5 pages.
Extended European Search Report dated May 14, 2014 for EP Patent Application No. 13192322.9.
First Technical Examination and Search Report dated Jun. 26, 2014 for DK Patent Application No. PA 2013 70667, 5 pages.
First Technical Examination and Search Report dated Jun. 27, 2014 for DK Patent Application No. PA 2013 70666.
Non-final Office Action dated Nov. 18, 2014 for U.S. Appl. No. 13/271,180.
Conway et al., Antennas for Over-Body-Surface Communication at 2.45 GHz, Apr. 2009, IEEE Transactions on Antennas and Propagation, vol. 57, No. 4, pp. 844-855.
Non-final Office Action dated Nov. 19, 2014 for U.S. Appl. No. 13/931,556.
Non-final Office Action dated Dec. 18, 2014 for U.S. Appl. No. 13/740,471.
Final Office Action dated Dec. 31, 2014 for U.S. Appl. No. 13/271,170.
Non-final Office Action dated Jan. 5, 2015 for U.S. Appl. No. 13/848,605.
Extended European Search Report dated Oct. 9, 2014 for EP Patent Application No. 14181165.3.
"Novelty Search including a Preliminary Patentability Opinion Report", in reference to P81007295DK02, dated Jul. 28, 2011. 8 pages.
"Novelty Search including a Preliminary Patentability Opinion Report", in reference to P81101358DK01, dated Jul. 28, 2011, 8 pages.
Non-final Office Action dated Jan. 15, 2015 for U.S. Appl. No. 14/199,511.
Non-final Office Action dated Feb. 5, 2015 for U.S. Appl. No. 14/198,396.
Non-final Office Action dated Feb. 24, 2015 for U.S. Appl. No. 14/202,486.

(56) References Cited

OTHER PUBLICATIONS

Notice of Allowance dated Mar. 5, 2015 for U.S. Appl. No. 13/917,448.
Notice of Allowance dated Apr. 24, 2015 for U.S. Appl. No. 13/931,556.
First Technical Examination and Search Report dated Mar. 9, 2015, for related Danish Patent Application No. PA 2014 70489.
Non-final Office Action dated May 7, 2015 for U.S. Appl. No. 13/271,180.
Advisory Action dated May 14, 2015 for U.S. Appl. No. 13/271,170.
Notice of Allowance and Fee(s) Due dated May 22, 2015 for U.S. Appl. No. 13/848,605.
Non-final Office Action dated Jun. 10, 2015 for U.S. Appl. No. 14/199,263.
Notice of Allowance and Fee(s) Due dated Jun. 18, 2015, for U.S. Appl. No. 13/917,448.
Communication pursuant to Article 94(3) EPC dated Mar. 16, 2015, for related European Patent Application No. 11 184 503.8, 12 pages.
Communication pursuant to Article 94(3) EPC dated Mar. 19, 2015, for related European Patent Application No. 11 184 507.9, 12 pages.
Non-final Office Action dated Jul. 1, 2015 for U.S. Appl. No. 14/199,070.
Final Office Action dated Jul. 15, 2015 for related U.S. Appl. No. 13/740,471.
Notice of Allowance and Fees Due dated Aug. 3, 2015 for related U.S. Appl. No. 13/931,556.
Non-final Office Action dated Aug. 17, 2015 for related U.S. Appl. No. 14/198,396.
Non-final Office Action dated Aug. 25, 2015 for related U.S. Appl. No. 14/202,486.
Notice of Allowance and Fee(s) Due dated Sep. 2, 2015 for related U.S. Appl. No. 14/199,511.
Notice of Allowance and Fee(s) Due dated Sep. 3, 2015 for related U.S. Appl. No. 13/848,605.
Notice of Allowance and Fee(s) Due dated Sep. 25, 2015 for related U.S. Appl. No. 13/271,170.
Notice of Allowance and Fee(s) Due dated Nov. 18, 2015 for related U.S. Appl. No. 13/931,556.
Final Office Action dated Nov. 18, 2015 for related U.S. Appl. No. 14/199,263.
Non-final Office Action dated Dec. 2, 2015 for related U.S. Appl. No. 13/271,180.
Notice of Allowance and Fee(s) Due dated Dec. 18, 2015 for related U.S. Appl. No. 13/917,448.
Notification of Reasons for Rejection dated Nov. 24, 2015 for related Japanese Patent Application No. 2014-228343, 8 pages.
Notice of Allowance and Fee(s) Due dated Feb. 16, 2016 for related U.S. Appl. No. 13/740,471.
Advisory Action dated Feb. 1, 2016 for related U.S. Appl. No. 14/199,263.
Notice of Allowance and Fees Due dated Mar. 3, 2016 for related U.S. Appl. No. 13/931,556.
Final Office Action dated Mar. 22, 2016 for related U.S. Appl. No. 14/202,486.
Notice of Allowance and Fee(s) due dated Mar. 23, 2016 for related U.S. Appl. No. 14/198,396.
Final Office Action dated Apr. 4, 2016 for related U.S. Appl. No. 13/271,180.
Final Office Action dated Apr. 15, 2016 for related U.S. Appl. No. 14/199,070.
Notice of Allowance and Fee(s) dated May 25, 2016 for related U.S. Appl. No. 14/199,263.
Notice of Allowance and Fee(s) dated Jun. 17, 2016 for related U.S. Appl. No. 13/917,448.
Non-final Office Action dated Sep. 15, 2011 for related U.S. Appl. No. 12/131,867.
Non-final Office Action dated Feb. 10, 2012 for related U.S. Appl. No. 12/131,867.
Final Office Action dated Aug. 23, 2012 for related U.S. Appl. No. 12/131,867.
Non-Final Office Action dated Mar. 7, 2014 for related U.S. Appl. No. 12/131,867.
Notice of Allowance and Fee(s) due dated Sep. 12, 2014 for related U.S. Appl. No. 12/131,867.
Advisory Action dated Jul. 26, 2016 for related U.S. Appl. No. 13/271,180.
Non-final Office Action dated Sep. 29, 2016 for related U.S. Appl. No. 14/461,983.
Notice of Allowance and Fee(s) due dated Oct. 5, 2016 for related U.S. Appl. No. 13/271,180.
Non-final Office Action dated Oct. 24, 2016 for related U.S. Appl. No. 14/199,070.
Notice of Allowance and Fee(s) due dated Oct. 25, 2016 for related U.S. Appl. No. 14/202,486.
IEEE 100, "The Authoritative Dictionary of IEEE Standards Terms," Seventh Edition, 2000, 12 pages.
K. Fujimoto, et al., "Small Antennas," Research Studies Press, Feb. 1987, 11 pages.
Carl E. Smith, et al., "Performance of Short Antennas" Proceedings of the I.R.E., Oct. 1947, 13 pages.
Kurt Ikrath, et al., "Performance of Trees as Radio Antennas in Tropical Jungle Resorts", Feb. 1972, 66 pages.
Constantine A. Balanis, "Antenna Theory," Third Edition, Analysis and Design, Wiley-Interscience, A John Wiley & Sons, Inc., Publication, 2005, 15 pages.
"The 1987 ARRL Handbook for the Radio Amateur," Published by: The American Radio Relay League, Newington, CT 06111, USA, 1986, Sixty-Fourth Edition, 5 pages.
U.S. Appl. No. 60/924,800, filed May 31, 2007, 62 pages.
Prosecution history of U.S. Pat. No. 8,300,863 (U.S. Appl. No. 12/342,241).
The 1987 ARRL Handbook for the Radio Amateur, Published by: The American Radio Relay League, 1986, Sixty-Fourth Edition, 10 pages.
IEEE 100, "The Authoritative Dictionary of IEEE Standards Terms," Seventh Edition, Dec. 2000, 3 pages.
H. Newton, "Newton's Telecom Dictionary," Twenty-second Edition, Feb. 2006, 3 pages.
File History for Inter-Parte-Review No. IPR 2015-00104.
File History for Inter-Parte-Review No. IPR 2015-00103.
Prosecution History of U.S. Appl. No. 90/013,592, filed Sep. 22, 2015.
Prosecution History of U.S. Appl. No. 90/013,189, filed Mar. 25, 2014.
European Communication pursuant to Article 94(3) EPC dated Dec. 20, 2016 for corresponding/related EP Patent Application No. 13192323.7, 4 pages.
Notice of Allowance and Fee(s) Due dated Feb. 16, 2017 for related U.S. Appl. No. 14/202,486.
Complaint dated Feb. 17, 2017 for U.S. District Court, District of Minnesota, Case No. 17-499, 14 pages.
Transcript of Bruce McNair for IPR2015-00103, IPR2015-00104, Jul. 21, 2015, 90 pages.
Declaration of professor Bruce McNair for IPR against U.S. Pat. No. 8,300,863, Sep. 9, 2014, 54 pages.
File History for Inter-Parte-Review No. IPR2015-01947, 678 pages.
File History for Inter-Parte-Review No. IPR2015-01948, 663 pages.
Final Office Action dated Jun. 21, 2017 for related U.S. Appl. No. 14/199,070.
First Amended Complaint filed Jun. 12, 2017 in the U.S. District Court, District of Minnesota, for Case No. 17-499, 26 pages.
Exhibit 3 of the First Amended Compliant for Non Patent Literature Document No. 2, cited herewith, dated Jun. 12, 2017, 65 pages.
Exhibit 4 of the First Amended Compliant for Non Patent Literature Document No. 2, cited herewith, dated Jun. 12, 2017, 60 pages.
Exhibit 8 of the First Amended Compliant for Non Patent Literature Document No. 2, cited herewith, dated Jun. 12, 2017, 55 pages.
Exhibit 9 of the First Amended Compliant for Non Patent Literature Document No. 2, cited herewith, dated Jun. 12, 2017, 56 pages.
Final Office Action dated May 19, 2017 for related U.S. Appl. No. 14/461,983.

(56) References Cited

OTHER PUBLICATIONS

Notification of First Office Action dated Feb. 21, 2017 for related Chinese Patent Application No. 201410641926.9, 16 pages.
Notification of First Office Action dated Jan. 16, 2017 for related Chinese Patent Application No. 201410643821.7, 14 pages.
Notice of Allowance and Fee(s) dated Sep. 27, 2017 for related U.S. Appl. No. 14/199,070.
Non-final Office Action dated Jan. 31, 2018 for related U.S. Appl. No. 15/641,133.

* cited by examiner

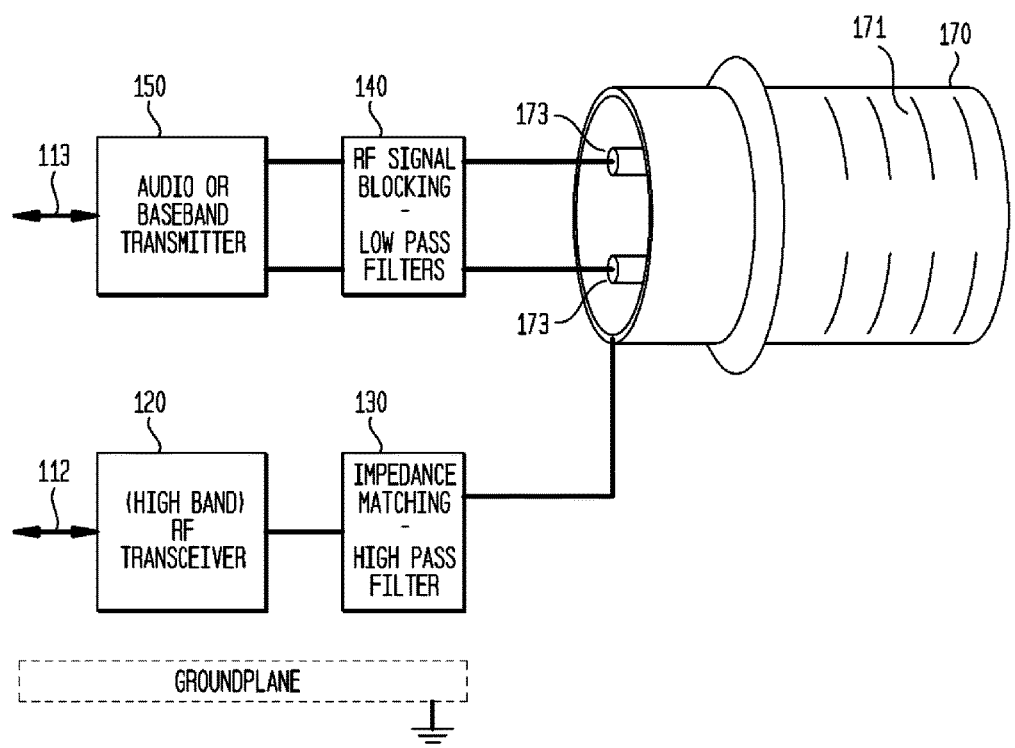

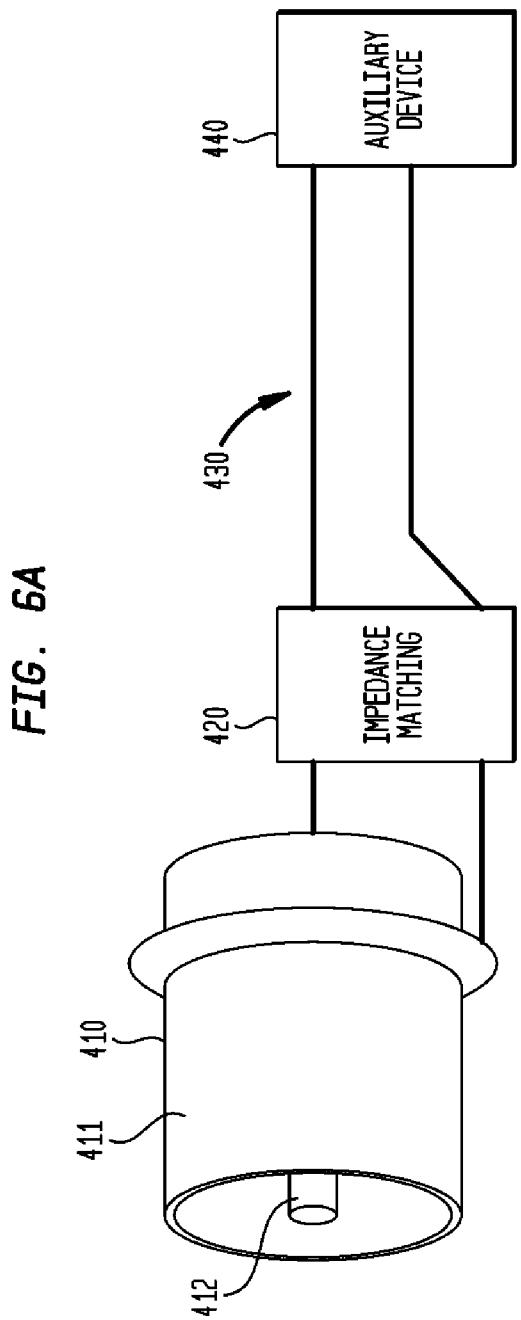

ACOUSTIC OUTPUT DEVICE WITH ANTENNA

RELATED APPLICATION DATA

This application is a continuation of U.S. patent application Ser. No. 15/188,780, filed Jun. 21, 2016, pending, which is a continuation of U.S. patent application Ser. No. 14/199,263, filed Mar. 6, 2014, now U.S. Pat. No. 9,446,233, which is a continuation of U.S. patent application Ser. No. 12/131,867, filed Jun. 2, 2008, now U.S. Pat. No. 8,934,984, and claims priority to U.S. Provisional Patent Application No. 60/924,800, filed on May 31, 2007, and U.S. Provisional Application No. 60/924,807, filed on May 31, 2007. All of the above-mentioned applications are hereby expressly incorporated by reference herein.

FIELD

The present disclosure relates generally to hearing prostheses and, more particularly, to a behind-the-ear (BTE) prosthetic device with an antenna.

BACKGROUND

Hearing aid prostheses, such as those designed to be worn behind the ear of the recipient, commonly referred to as behind-the-ear (BTE) devices, may be components of conventional hearing aids, cochlear implants, and/or the like. BTE devices, whether implemented as a component of a hearing aid, cochlear implant, middle ear implant or other hearing prosthesis, are collectively and generally referred to herein as a BTE prosthetic devices.

Conventional hearing aids may include external sound processors which input the processed (and amplified) sound in the ear by an external, or in-the ear speaker. Cochlear implants have been developed to assist people who are profoundly deaf or severely hearing impaired, by enabling them to experience a hearing sensation representative of the natural hearing sensation. In most such cases, these individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally comprised two parts, an external component and an implanted receiver/stimulator unit. The external component may be been worn on the body of a recipient, classically as a BTE prosthetic device. The purpose of such a BTE prosthetic device has been to detect external sound using a microphone and convert the detected sound into a coded signal through an appropriate speech processing strategy.

This coded signal is then sent via a transcutaneous link to receiver/stimulator unit which is implanted in the mastoid bone of the recipient. A transcutaneous link is a magnetic induction link between a coil antenna of the implant and an externally applied coil antenna. The receiver/stimulator unit processes the coded signal into a series of stimulation sequences which are then applied directly to the auditory nerve via a series of electrodes positioned within the cochlea proximal to the modiolus of the cochlea.

The externally applied coil antenna typically forms part of a headpiece, which is applied in close proximity of the coil antenna of the implant and is connected to an external speech processor, such as a device for behind the ear. The magnetic induction link (established in a reactive near-field) typically allows bidirectional communication and power transfer towards the implant.

SUMMARY

In accordance with aspects, a behind-the-ear (BTE) prosthetic device for use in a medical system is provided. The BTE prosthetic device comprises: a connector configured to mechanically attach an auxiliary device to the BTE prosthetic device; and a transceiver comprising one or more of an RF transmitter and an RF receiver, wherein the connector is electrically connected to the RF transceiver, and wherein the connector operates as an electromagnetic antenna for wireless communication between the BTE prosthetic device and one or more other components of the system.

In accordance with other aspects, a cochlear implant system is provided. The cochlear implant system comprises: an implantable component; an external auxiliary component; and a behind-the-ear (BTE) prosthetic device comprising: a connector configured to mechanically attach said auxiliary device to said BTE prosthetic device; and an transceiver comprising one or more of an RF transmitter and an RF receiver, wherein said connector is electrically connected to said transceiver, and wherein said connector is configured to operate as an electromagnetic antenna for wireless communication between said BTE prosthetic device and said implantable component.

In accordance with other aspects, a hearing device is provided. The hearing device comprises a first portion configured to be arranged at a head of a user and to provide a signal to a second portion; the second portion configured to be arranged in an ear or an ear canal of the user and to provide acoustic output to the user, the second portion including a transducer for converting the signal into the acoustic output; an antenna for wireless communication, the antenna comprising an electrically conducting element; and a coupling element coupling the first portion and the second portion, the coupling element comprising the electrically conducting element.

In accordance with other aspects, a hearing device is provided. The hearing device comprises a first portion configured to be arranged at a head of a user and to provide a signal to a second portion; the second portion configured to be arranged in an ear or an ear canal of the user and to provide acoustic output to the user, the second portion including a transducer for converting the signal into the acoustic output; a coupling element coupling the first portion and the second portion, the coupling element configured to transmit the signal from the first portion to the second portion, the coupling element including an electrically conducting element; wherein the electrically conducting element in the coupling element is configured to operate as a part of an antenna for wireless communication.

A hearing aid includes: a hearing aid component configured to be arranged at a head of a user, and away from an ear canal of the user, the hearing aid component configured to provide a signal to an earpiece; the earpiece configured to be arranged at the ear of the user, and configured to provide an acoustic output to the user; and a coupling element configured for coupling the hearing aid component and the earpiece, the coupling element having a tube and an electrically conducting element; wherein the electrically conducting element in the coupling element of the hearing aid is configured to operate as a part of an antenna for wireless communication, and wherein the electrically conducting element is configured for electromagnetic signal emission and/or electromagnetic signal reception.

Optionally, the electrically conducting element is configured to transmit the signal from the hearing aid component to the earpiece.

Optionally, the hearing aid further includes a speaker at the earpiece, wherein the coupling element of the hearing aid comprises two wires coupled to the speaker at the earpiece, and wherein the electrically conducting element comprises at least one of the two wires.

Optionally, the coupling element comprises an additional electrically conducting element for transmitting the signal from the hearing aid component to the earpiece, and wherein the electrically conducting element is a dedicated antenna for the wireless communication.

Optionally, the hearing aid component comprises a wireless communication interface for receiving and/or sending data through the antenna.

Optionally, the hearing aid further includes a microphone at the hearing aid component.

Optionally, the electrically conducting element comprises one or more conductors configured for wireless communication of data, and for transmission of the signal from the hearing aid component to the earpiece.

Optionally, the electrically conducting element is configured for wireless communication of data and for transmission of the signal in different respective frequency bands.

Optionally, the hearing aid component comprises a wireless communication component and a tuning circuit configured to tune the electrically conducting element in correspondence with the wireless communication component.

Optionally, the coupling element of the hearing aid comprises a connector for connection to the hearing aid component.

Optionally, the hearing aid component comprises a hearing aid housing shaped for worn outside the ear of the user.

Optionally, the hearing aid component comprises a behind-the-hear housing.

Optionally, the earpiece comprises at least a portion sized for insertion into the ear canal of the user.

Optionally, the coupling element of the hearing aid comprises a cable connected between the hearing aid component and the earpiece.

A hearing aid includes: a behind-the-ear (BTE) unit configured to be arranged at a head of a user, and away from an ear canal of the user, the BTE unit comprising a microphone and a control for facilitating interaction of the user with the hearing aid, wherein the hearing aid component is configured to provide a signal to an earpiece; the earpiece configured to be arranged at the ear of the user, and configured to provide an acoustic output to the user; and a coupling element configured for coupling the BTE unit and the earpiece, the coupling element having an electrically conducting element; wherein the electrically conducting element in the coupling element of the hearing aid is configured to operate as a part of an antenna for wireless communication, and wherein the electrically conducting element is configured for electromagnetic signal emission and/or electromagnetic signal reception.

Optionally, the electrically conducting element is configured to transmit the signal from the BTE unit to the earpiece.

Optionally, the hearing aid further includes a speaker at the earpiece, wherein the coupling element of the hearing aid comprises two wires coupled to the speaker at the earpiece, and wherein the electrically conducting element comprises at least one of the two wires.

Optionally, the coupling element comprises an additional electrically conducting element for transmitting the signal from the BTE unit to the earpiece, and wherein the electrically conducting element is a dedicated antenna for the wireless communication.

Optionally, the electrically conducting element comprises one or more conductors configured for wireless communication of data, and for transmission of the signal from the BTE unit to the earpiece.

Optionally, the hearing aid component comprises a wireless communication component and a tuning circuit configured to tune the electrically conducting element in correspondence with the wireless communication component.

Other features, advantageous, and embodiments will be described in the detailed description.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

Illustrative embodiments are described herein with reference to the accompanying drawings, in which:

FIG. 3B illustrates a twin-axial male connector in accordance with one embodiment;

FIG. 6A illustrates a co-axial connector in accordance with one embodiment;

DETAILED DESCRIPTION OF THE DRAWINGS

Various illustrative examples of the new hearing device according to the appended claims will now be described more fully hereinafter with reference to the accompanying drawings, in which various embodiments of the new hearing device and method are illustrated. The new hearing device according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described.

Aspects of the present embodiments are generally directed to a connector for a prosthesis configured to be worn behind the ear of an individual or recipient, commonly referred to as behind-the-ear (BTE) devices. BTE devices may be a component of a conventional hearing aid and/or cochlear implant, or a component of any other medical systems or prosthesis. BTE devices, whether implemented as a component of a hearing aid, cochlear implant, middle ear implant or other medical systems/prosthesis, are collectively and generally referred to herein as a BTE prosthetic devices.

In certain aspects, a BTE prosthetic device for use in a medical system or prosthesis, (collectively and generally referred to as medical systems herein) comprises a connector configured to mechanically attach an auxiliary device of the system to the BTE prosthetic device. The connector is electrically connected to a transceiver of the BTE prosthetic device. The transceiver may comprise any combination of a transmitter and/or an receiver. Furthermore, the transceiver may comprise only a transmitter or a receiver. The connector is configured to operate as an electromagnetic antenna for transmitting and/or receiving signals between the BTE prosthetic and other components of the medical system. The electromagnetic antenna may be, for example, operable in the far-field.

Figure 1:
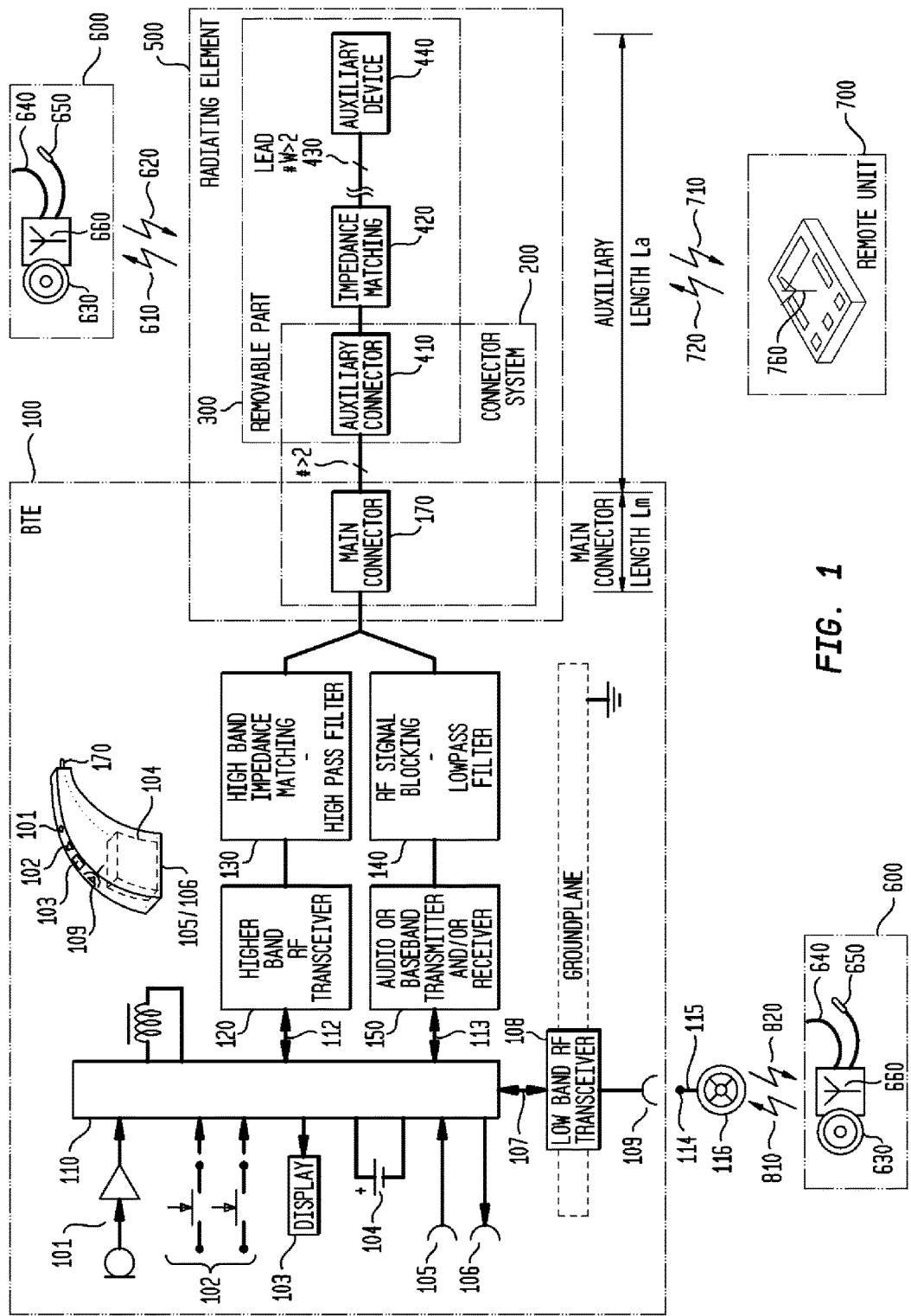
FIG. 1 is a schematic block diagram of a behind-the-ear (BTE) prosthetic device having an integrated antenna and connector.

As noted, embodiments may be implemented with a number of BTE prosthetic devices in a variety of medical systems. Embodiments will be described herein with reference to one specific type of BTE prosthetic device and medical system, namely a BTE prosthetic device which is a component of a partially implantable hearing aid system. FIG. 1 illustrates such a partially implantable hearing aid system, comprising BTE prosthetic device 100 in communication with one or more cochlear stimulating implants, shown generally as implants 600 and one or more remote units 700. Implants 600 may each comprise a variety of implantable cochlear stimulating devices, such as an implantable electrode arrays, middle ear implants, or the like. As described in more detail below, BTE prosthetic device 100 may communicate with other components of the partially implantable hearing aid system via one or more wireless communication links, shown as communication links 610, 620, 710, 720, 810 and 820.

In the illustrated embodiment of FIG. 1, BTE prosthetic device 100 comprises a microphone 101 to receive acoustic sounds, and a signal processor 110. BTE prosthetic device 100 converts and processes the received acoustic sounds received by microphone 101, or various other received auditory signals, to a format which may used by the implants 600. In accordance with the illustrated embodiments, BTE prosthetic device 100 further comprises one or more transceivers 108 which may transmit processed signals to implants 600.

BTE prosthetic device 100 has sufficient persistent and non-persistent memory. Furthermore, BTE prosthetic device 100 is powered by a battery 104. Additional controls 102 and interfaces 103 facilitate human interaction with the hearing aid system. In certain embodiments, the main housing of BTE prosthetic device 100 may accept removable plug-in modules, such as batteries, an ear hook, a headpiece, etc. BTE prosthetic device 100 may also be provided with input and output jacks 105 and 106.

As noted, a variety of cochlear stimulating implants may be used in accordance with some embodiments. FIG. 1 illustrates specific implants 600 which comprise an implantable electrode array 640 that stimulate the recipient's cochlea with electrical signals. The implant converts the signals received from the BTE prosthetic device 100 into stimuli signals and then applies them to the cochlea via electrode array 640. Depending on cause of the recipient's deafness, implant 600 may optionally comprise a mechanical implantable actuator 650 configured to stimulate middle or inner ear parts, in addition to, or in place of, electrode array 640.

In some embodiments, BTE prosthetic device 100 comprises a lower radio frequency (RF) band transceiver 108 for wireless communication over a magnetic induction link, such as links 810 and 820. Transceiver 108 may be configured to transmit and/or receive wireless communications. Low RF band transceiver 108 may be connected, in certain embodiments, to a connector socket 109, which accepts a plug 114 of a headpiece 116. Headpiece 116 comprises an extension cable 115 between plug 114 and an antenna coil or closed-wire loop 116. Antenna coil 116 is configured to transmit signals to coil antenna 630 of an implant 600, and/or receive signals from coil antenna 630. Antennas 116 and 630 may be placed in close proximity of each other.

The above-described communication link 810 and 820 between BTE prosthetic device 100 and implant 600 operates in the reactive near-field, by magnetic induction in a non-propagating quasi-static magnetic field. Both bidirectional data transfer and power transfer towards the implant are possible.

In accordance with certain embodiments, communication between components of a medical system may occur in a near-field or far EM-field, via, for example, electromagnetic field propagation. This type of communication has the advantage that it takes place over larger distances, which would permit components of the communication link to be spaced apart by larger distances than permitted in a conventional RF link. Furthermore, wireless communication between the BTE prosthetic device 100 and other external devices 700 may also preferably take place in the propagating far-field. An antenna tuned to the frequency range of operation is generally used for efficient communication using the EM-field. Whereas a magnetic induction link uses a coil or closed-wire antenna, transmission and reception by electromagnetic field propagation may be carried out with open-ended antennas.

Figure 2A:
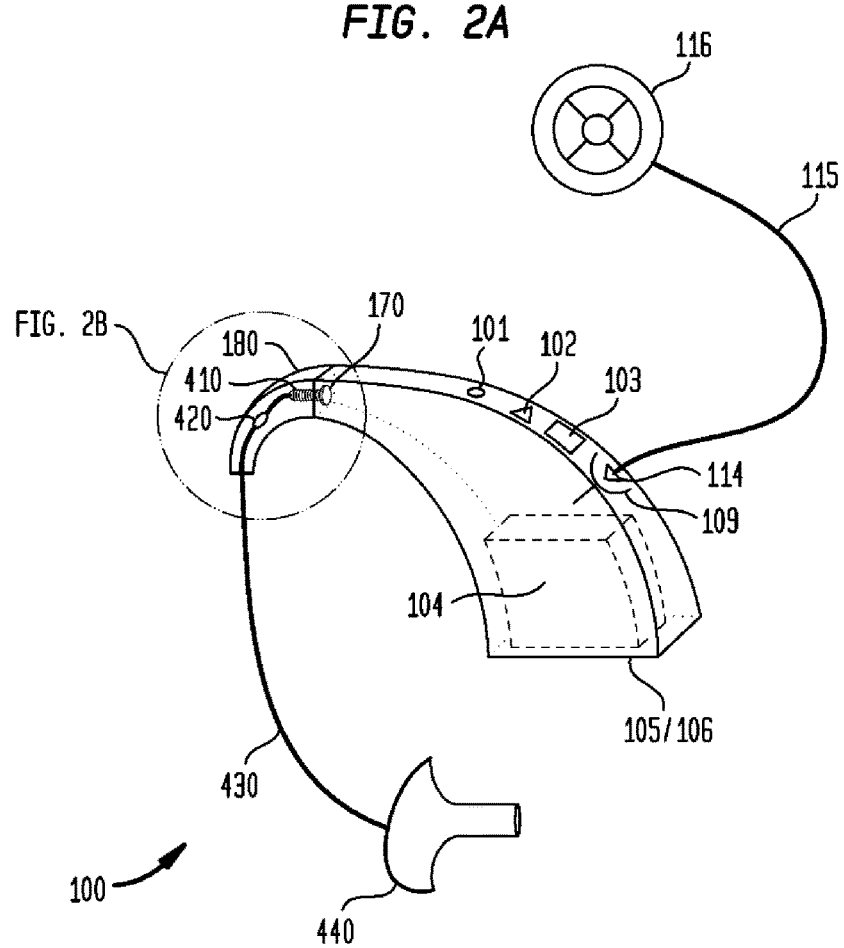
FIG. 2A illustrates a BTE prosthetic device having an ear hook and auxiliary device with extension antenna in accordance with embodiments.
Figure 2B:
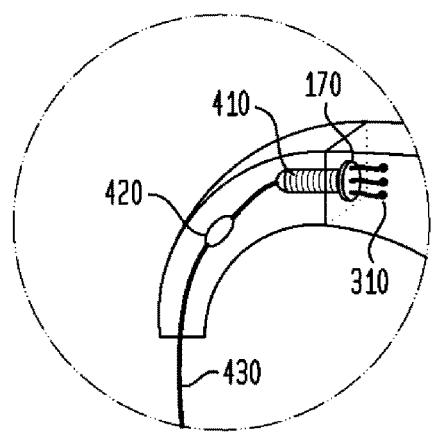
FIG. 2B illustrates a close-up view of a portion of the BTE prosthetic device of FIG. 2.

According to some aspects, an electromagnetic antenna is integrated with a mechanical connector which is used in BTE prosthetic device 100 to mechanically attach various components or other devices to the BTE prosthetic device. According to one embodiment, and referring to FIGS. 1 and 2, an electromagnetic antenna can be incorporated into a connector, shown as connector 170. In the specific illustrated embodiment of FIGS. 1 and 2, connector 170 of the BTE prosthetic device 100 is configured to mechanically attach an ear hook 180 to BTE prosthetic device 100. Connector 170 may also be configured to operate as, or function as, as an electromagnetic antenna for transmission of, or reception of signals between BTE prosthetic device 100 and one or more other components of the implantable hearing system.

Ear hook 180 provides a mounting means for holding BTE prosthetic device 100 behind the ear of the recipient. Connector 170 may include, for example, threaded attachment elements, a snap-lock or click-fit mechanism or any other removable mechanical fastening means now know or later developed for attaching connector 170 to BTE prosthetic device 100. In certain embodiments, one or more conducting wires 310 provide an electrical coupling between connector 170 and components of BTE prosthetic device 100, such as the printed circuit board of the BTE prosthetic device.

As noted, connector 170 may also be configured for electrical connection with an auxiliary device. For example, connector 170 may be provided with, or comprise, for example, a socket accepting a plug 410 of an auxiliary device 440, such as an earphone.

Figure 3A:
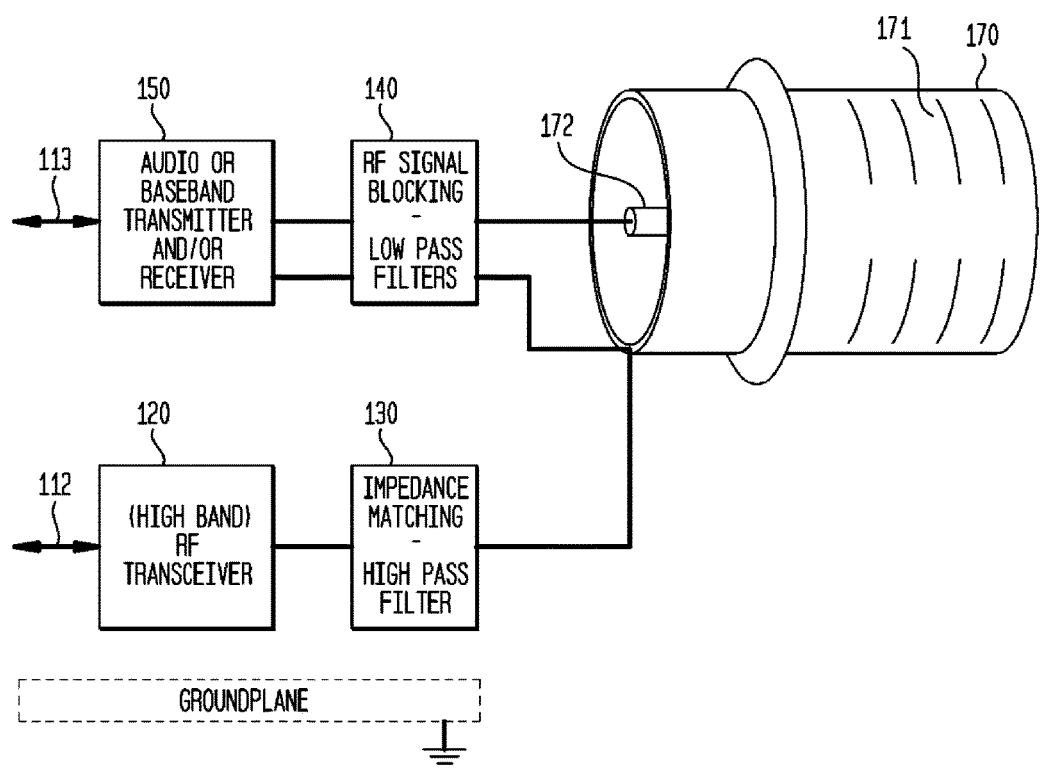
FIG. 3A illustrates a co-axial male connector in accordance with one embodiment.

Some possible embodiments of connector 170 are illustrated in FIG. 3. FIG. 3A illustrates connector 170 as a coaxial electrical and mechanical connector type. FIG. 3B illustrates connector 170 as a twin-axial electrical and mechanical connector type. In certain embodiments, connector 170 may comprise an outer body 171 which is cylindrical and may be made of an electrical conducting material.

In the embodiments of FIG. 3A, coaxial connector 170 comprises one electrically conductive receptacle 172, in addition to the conductive outer body 171. Hence, the outer body 171 and the receptacle 172, which are electrically shielded from each other, constitute an input or output jack for transmitting and/or receiving electrical signals, such as audio signals, to and from the attached auxiliary device 440. Therefore, BTE prosthetic device 100 may comprise an audio or baseband transmitter and/or receiver (transceiver) 150, linked at 113 to signal processor 110. Audio/baseband transceiver 150 is connected to the outer body 171 and to the receptacle 172 of connector 170.

The outer body 171 is configured to operate as, or function as, as part of an electromagnetic antenna for transmitting or receiving signals. As noted, connector 170 may be used by BTE prosthetic device 100 to transmit, or receive signals from, one or more other components of the implantable hearing system. In certain embodiments, outer body 171 operates as an open-ended wire, a monopole, stub, helix or helical wound coil, meander or dipole electromagnetic antenna. The electromagnetic antenna is operable in a variety of frequency ranges, including above 100 KHz, and in some embodiments in a frequency range above 30 MHz or 3 GHZ. As such, in the illustrated embodiments, connector 170 is configured for electrical connection of an auxiliary device to BTE prosthetic device 100 and for transmission and/or reception of signals between components of the hearing aid system.

BTE prosthetic device 100 may comprise an RF high band transceiver 120, linked via link 112 to signal processor 110. RF transceiver 120 is connected to the outer body 171. In order to improve the reception or transmission of power efficiency of outer body 171 as an antenna, an impedance matching circuit 130 may be provided between transceiver 120 and outer body 171. A high-pass or band-pass filter 130 and a low-pass or band-pass filter 140 ensure a separation of the radiated RF signals and the signals transferred over the jack combination 171/172. Hence, filter 140 blocks high RF band signals and prevents them from propagating to the transceiver 150 and high-pass filter 130 blocks low band signals (e.g. audio, baseband) and prevents them from leaking into transceiver 120.

Connector 170 may comprise multiple separate electrical conduction paths for conductive transmission of electrical signals. Likewise, outer body 171 of connector 170 may or may not transfer electrical signals. In certain embodiments, connector 170 protrudes from BTE prosthetic device 100.

FIG. 3B illustrates an additional embodiment. As shown, the twin-axial connector 170 of FIG. 3B comprises two electrically conductive receptacles 173, in addition to a conductive outer body 171. Hence, the receptacles 173, which are electrically shielded from each other, constitute a jack for transmitting and/or receiving electrical signals, such as audio signals, to and from an auxiliary device 440 attached thereto. Therefore, BTE prosthetic device 100 may comprise an audio or baseband transmitter and/or receiver (transceiver) 150, linked at link 113 to signal processor 110. Audio/baseband transceiver 150 is connected to the receptacles 173.

In the embodiments of FIG. 3B, the outer body 171 may operate as an electromagnetic antenna similar to that described above with reference to FIG. 3A. Therefore, BTE prosthetic device 100 may comprise a high RF band transceiver 120, linked at link 112 to signal processor 110. RF transceiver 120 is connected to the outer body 171. In certain embodiments, to improve receive or transmit power efficiency of the antenna, an impedance matching circuit 130 is provided between transceiver 120 and the antenna (outer body) 171 for making the impedance of the antenna, as seen by the transceiver, real. A high-pass or band-pass filter 130 and a low-pass or band-pass filter 140 may ensure a separation of the radiated RF signals and the signals transferred over the jack 173. The low-pass and high-pass filters may be optional in the case of FIG. 3B, as the two types of signals (to/from transceivers 150 and 120) may not share the same electrical paths as in the case of FIG. 3A. However, radiated RF signals may be captured by the receptacles 173 and may interfere with the operation of the baseband transceiver 150. Likewise, the antenna 171 may capture low band signals. Hence, filter 140 blocks high RF band signals and prevents them from propagating to the transceiver 150 and high-pass filter 130 blocks low band signals and prevents them from leaking to transceiver 120.

A low band signal preferably comprises frequencies below or equal to about 100 KHz, while high RF band signals comprise signals situated in the radio spectrum above 100 KHz, such as, for example, 2.4 GHz. For the purposes of the present embodiments, high RF band signals are signals in the VHF (very high frequency), UHF (ultra high frequency), or higher frequency range. The low-pass filter 140 and the high-pass filter 130 may function as a band diplexer. The antenna 170 may be arranged to transmit or receive data such as telemetry, control data, signalling data and audio streaming.

Figure 4:
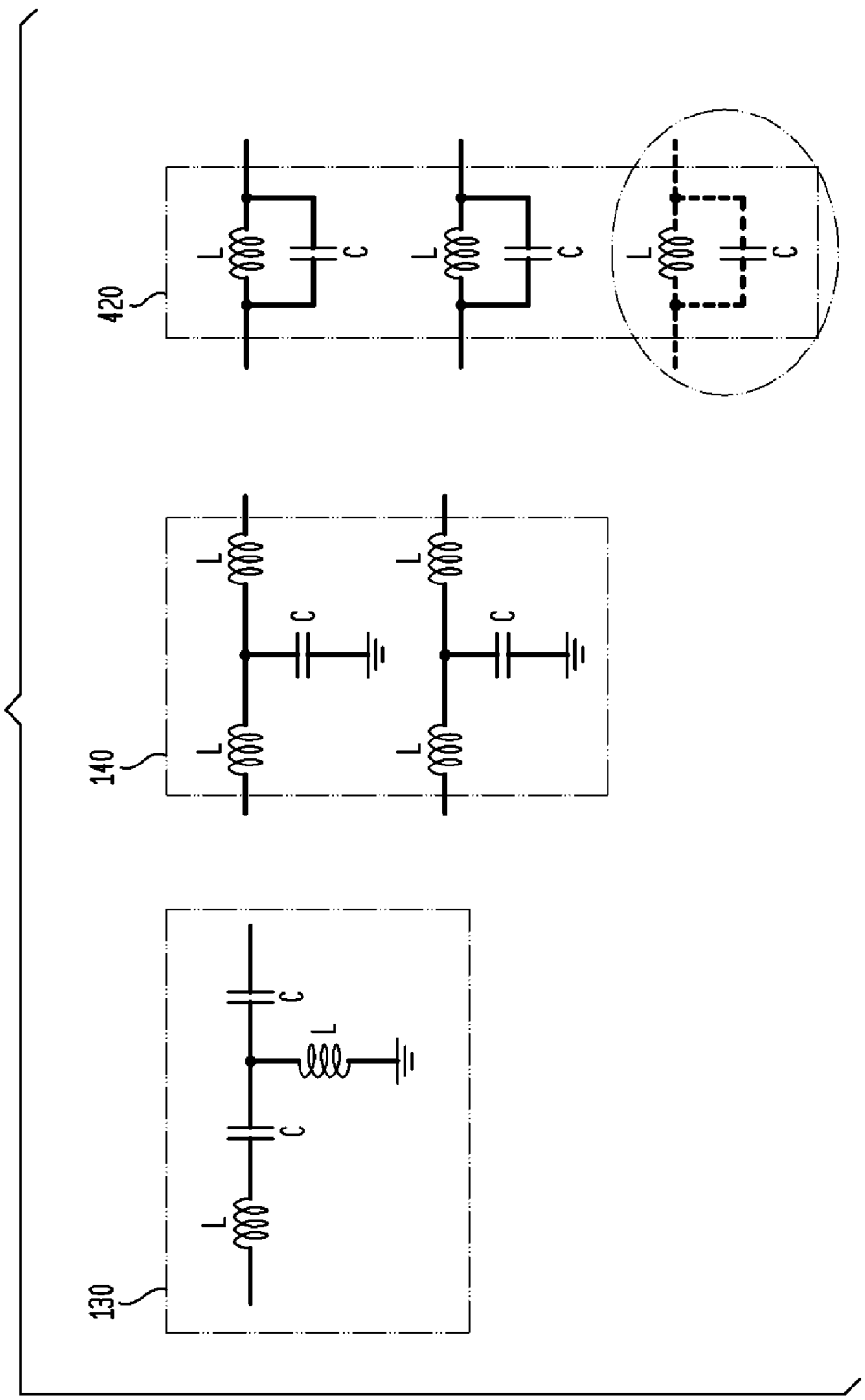
FIG. 4 illustrates embodiments of antenna impedance matching units and low-pass and high-pass filters in accordance with some embodiments.

FIG. 4 illustrates a possible implementation of the impedance matching circuit and high-pass filter 130 and the low-pass filter 140 in accordance with some embodiments. As shown in FIG. 4, such filters may comprise, for example, lumped resistors, capacitors and inductors, or other elements now know or later developed, the values of which may be chosen in function of the operating frequencies of the devices. The audio or baseband signals applied to or received from the auxiliary device are much lower in frequency than the RF signals radiated by the antenna. A third-order filtering may be sufficient in most cases.

Antenna impedance matching circuit 130 may be used to alter the effective electrical length of an antenna by matching it with additional capacitance or inductance. Antenna impedance matching circuit 130 tunes the radiating system of the antenna at the operational radio frequency, in order to obtain resonance. In one such case, the RF transceiver 120 sees the antenna as a purely resistive load. Such a matching circuit is optional.

Figure 5:
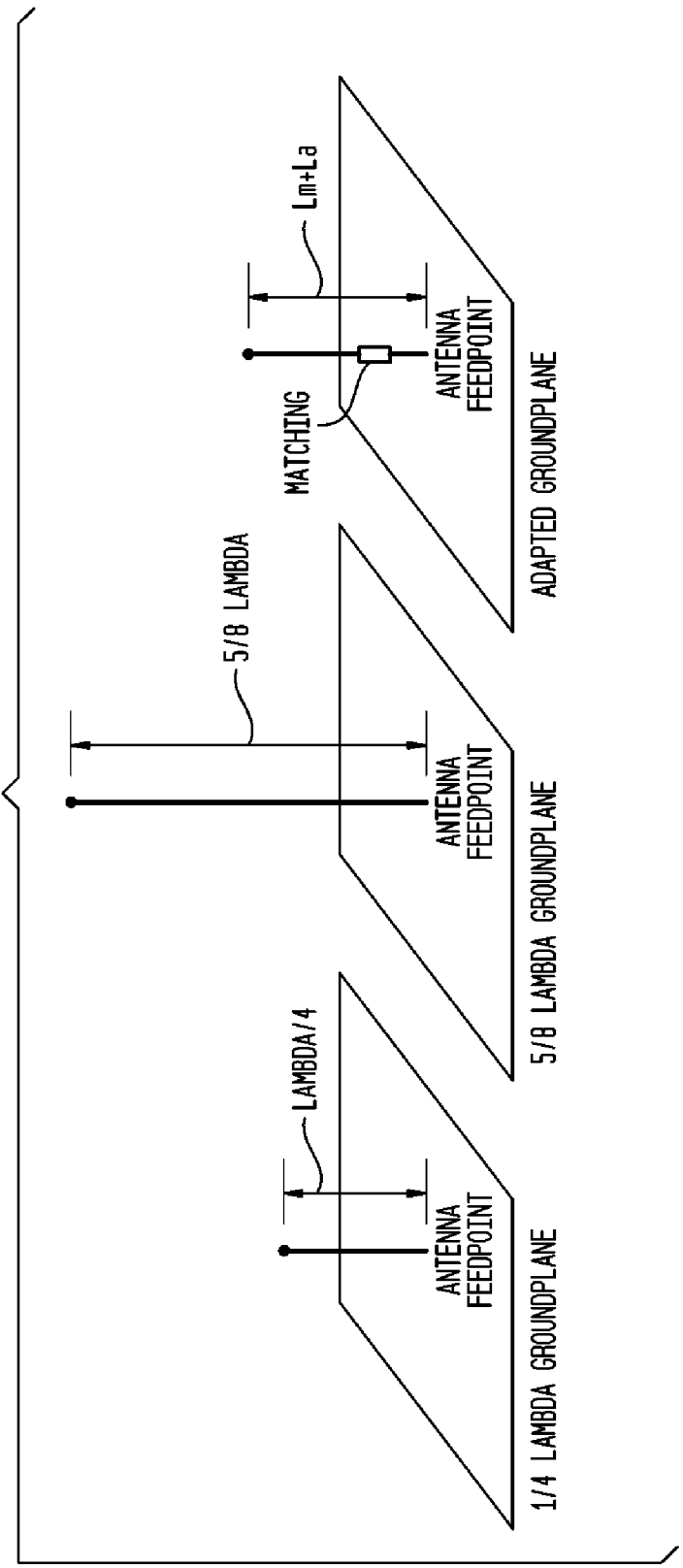
FIG. 5 schematically illustrates different matched ground plane antennas.

As noted, antenna 171 may operate as an open-ended wire antenna, such as a monopole, a dipole, a groundplane, a helix, a helical wound, or a meander antenna. FIG. 5 shows a simplified representation of a quarter λ, a ⅝λ and a matched groundplane antenna. The physical construction of antenna 171 of the present embodiments can be considered as a groundplane antenna, with the housing of BTE prosthetic device or its printed circuit board as ground plane element and the connector 170 as radiating or receiving element. From an antenna-matching viewpoint, it is preferable to choose the total physical length of the antenna (e.g. the length of the outer body 171 of connector 170) to λ/4 or ⅝λ, with λ the wavelength of the operating frequency of the antenna.

When the wavelength is very small, e.g. at 2.4 GHz, antenna matching is performed on the connector 170. At lower frequencies, an antenna with increased physical length is used. This may be achieved by incorporating, for example, into the auxiliary device which is attached to the BTE prosthetic device, an extension of antenna 170. Such an arrangement is illustrated in FIG. 1 with device 300.

In the illustrated embodiments, device 300 comprises all elements necessary for operation as an electromagnetic antenna, such as a ground plane and radiating/receiving elements. As such, device 300 is referred to as an auxiliary antenna device. The auxiliary antenna device 300 may be removably attached to the BTE prosthetic device 100 and comprises a connector plug 410 for acceptance by connector 170, the auxiliary device 440, a lead 430 between connector and auxiliary device and an optional antenna impedance matching circuit 420. The lead 430 is a naturally preferred object for use as radiating/receiving element and lends itself as an extension of antenna 170.

When auxiliary antenna device 300 is coupled to connector antenna 170, an antenna 500 is obtained with increased length over the antenna provided by connector antenna 170 alone. The total physical length of antenna 500 is the sum of the length Lm of the connector 170 (base antenna) and the length La of auxiliary antenna 300. The auxiliary antenna device 300 may comprise a matching circuit 420 in additional to the matching circuit 130 of connector 170.

The integration of a removable auxiliary antenna allows to improve radiating efficiency due to a physical extension of the radiating element. The auxiliary antenna devices 300 may allow antennas matched for different operating frequencies. The auxiliary antenna devices 300 may additionally allow antennas of different physical lengths for a same operating frequency. In the latter case, because of the different physical lengths, different impedance matching circuits should be implemented. Such embodiments, allow BTE prosthetic device 100 to be very versatile in the field of wireless communication and communicate with different devices over different RF bands.

Figure 6B:
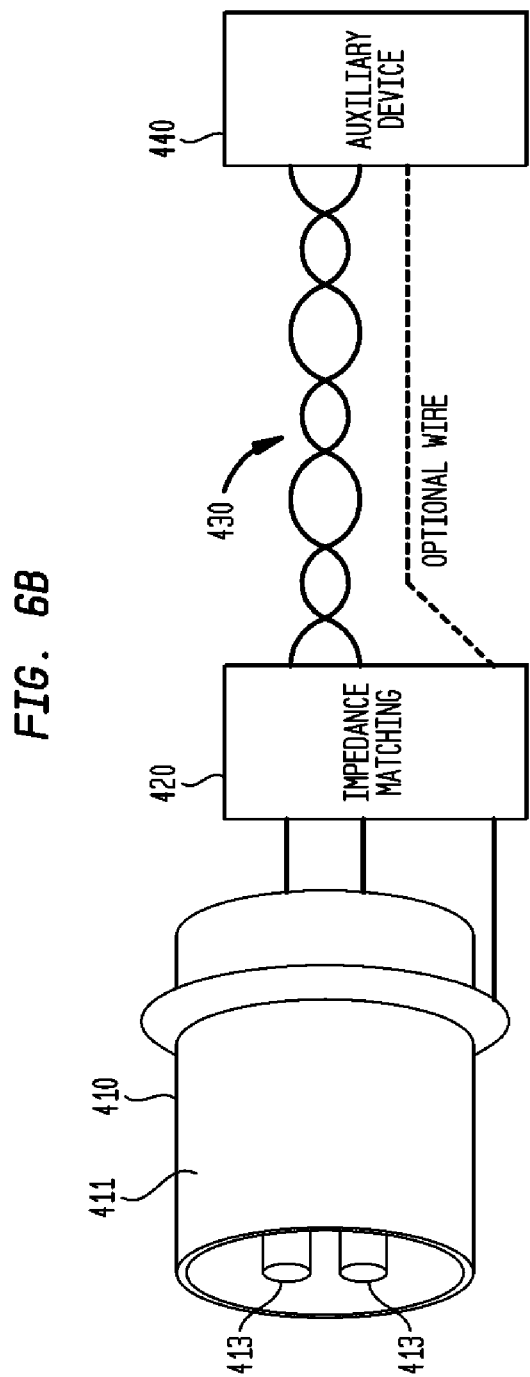
FIG. 6B illustrates a twin-axial connector in accordance with one embodiment.

FIGS. 6A and 6B generally illustrates the components of auxiliary antenna device 300 in accordance with certain embodiments. Coaxial connector plug 410 of FIG. 6A is arranged for fitting into coaxial connector socket 170 of FIG. 3A. The twin-axial connector plug 410 is configured to fit into twin-axial connector socket 170 of FIG. 3B. A lead 430 comprising two or more conductive wires links connector plug 410 and impedance matching circuit 420, such as any of those shown in FIG. 4, to the auxiliary device 440. Lead 430 may conduct low-band electrical signals (e.g. audio signals) from BTE prosthetic device 100 to the auxiliary device 440 or vice versa.

In the case of a coaxial connector system 200, comprising socket 170 and plug 410 (FIGS. 3a and 6a), electrical connection with BTE prosthetic device 100 is obtained by electrical contact between receptacle 172 and plug 412, and between the outer bodies 171 and 411 of the connectors. In the case of a twin-axial connector system 200, comprising socket 170 and plug 410 (FIGS. 3b and 6b), the electrical connection with the BTE prosthetic device is obtained by electrical contact between the two receptacles 173 and plugs 413, and optionally additionally between the outer bodies 171 and 411 of the connectors.

Returning to FIG. 1, antenna 170, or the extended antenna 500, allows wireless communication in a radio frequency band between a BTE prosthetic device 100 and remote devices. Such devices may be a remote control unit 700, provided with an antenna 760 for wireless communication in the same frequency band. A bidirectional wireless communication link 710, 720 may be established between BTE prosthetic device 100 and remote control unit 700. The BTE prosthetic device 100 may also communicate wirelessly with cochlear implant 600, both through a magnetic induction link 810, 820 by aid of headpiece 116, and through a radio frequency electromagnetic link 610, 620 by the use of antennas 500 or 170 of the BTE prosthetic device and RF antenna 660 of the cochlear implant.

Figure 7:
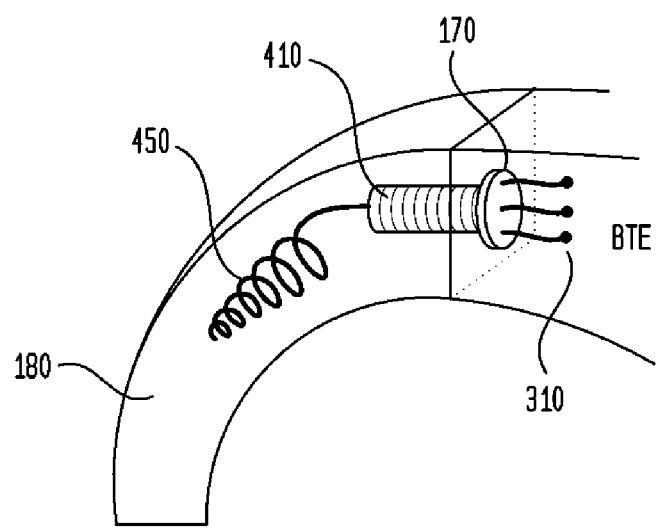
FIG. 7 illustrates a BTE prosthetic device having an ear hook mechanically attached thereto via a connector in accordance with some embodiments.

FIG. 7 illustrates an additional embodiment for an auxiliary antenna device 450 for use as extension of antenna 170. Antenna 450 is constituted by a helically wound antenna, and is incorporated into ear hook 180.

In accordance with certain embodiments, an auxiliary device may comprise an external plug-in device, such as an in-the-ear speaker. According to other aspects, an antenna device comprises a second connector for fitting into the connector of BTE prosthetic device 100, an impedance matching circuit and a lead. The impedance matching circuit is tuned to the impedance of the lead, whereby the lead is operable as an extension of the electromagnetic antenna. The second connector is the counterpart of the connector of the hearing aid device. The second connector may be a plug or a socket.

Figure 8:
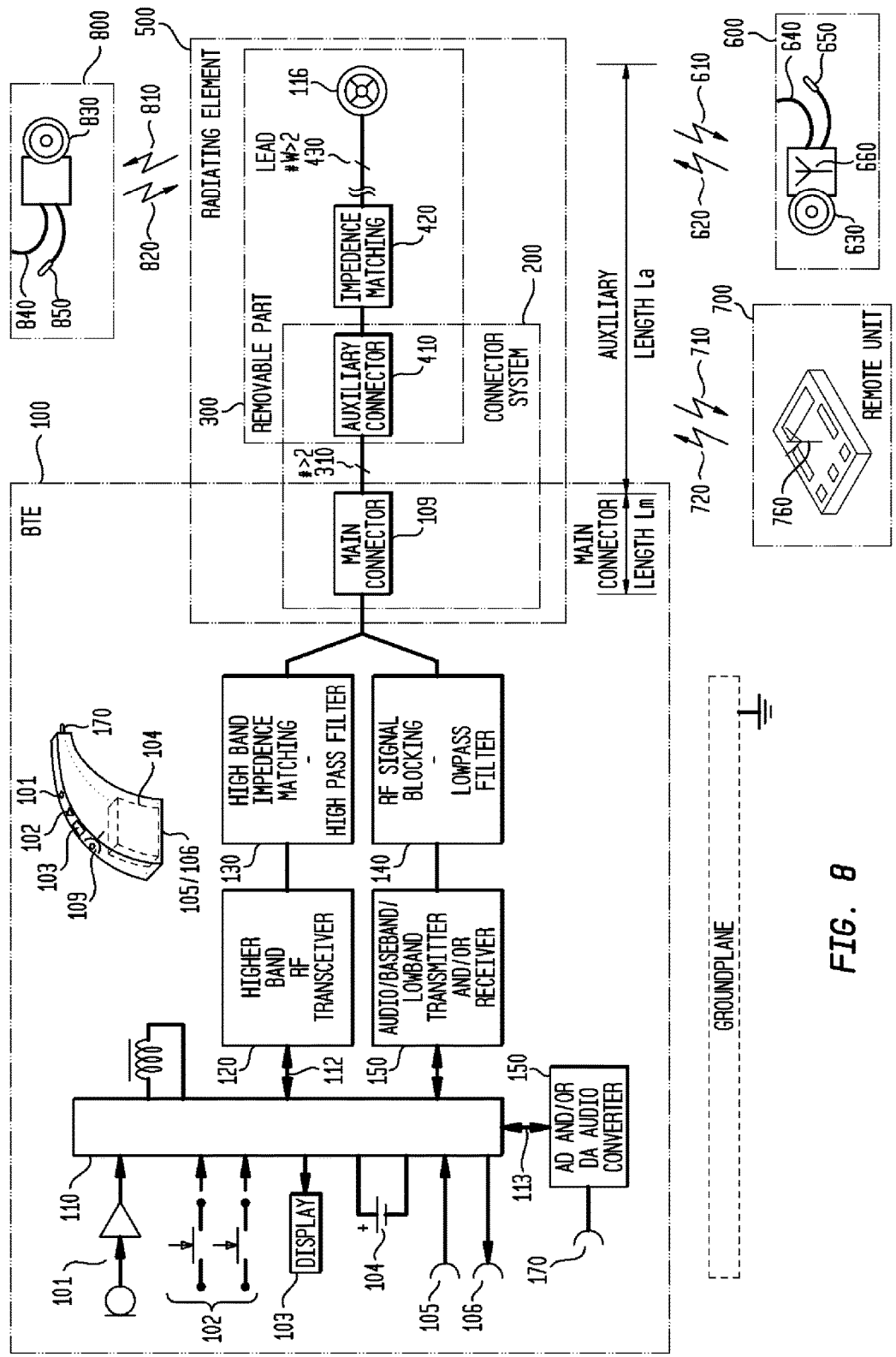
FIG. 8 is a block diagram of a BTE prosthetic device in accordance with some embodiments.

The antenna in accordance with some embodiments is not only restricted to connector 170 of an ear hook. FIG. 8 shows an alternative embodiment wherein the antenna is incorporated into connector socket 109 of headpiece 116. In such embodiments, connector socket 109 may be implemented in a substantially similar manner as that described above with reference to connector socket 170. In the specific embodiments in which headpiece 116 is additionally used as an auxiliary RF antenna device, the removable device 300 may comprise an auxiliary connector 410 arranged for being accepted by connector 109, an impedance matching unit 420 and a headpiece 116, connected to the auxiliary connector 410 by a lead comprising two or more wires.

As discussed above with reference to FIG. 1, the BTE prosthetic device 100 may communicate wirelessly with an implant 600, which is provided with both a magnetic induction coil antenna 630 and an RF EM-field antenna 660. Coil antenna 630 may communicate with headpiece 116 when closely coupled. Communication over RF antennas 500 and 660 may be established simultaneously, or consecutively in time with the communication over antennas 116 and 630.

In the case that a implant, such as implant 800, is not provided with an RF antenna, wireless communication between BTE prosthetic device 100 and cochlear implant 800 may be established over a magnetic induction link 810, 820 using coil antennas 116 and 830, e.g. for transmitting stimuli signals to an electrode array 840 and/or actuator 850. Simultaneously, the BTE prosthetic device may communicate over antenna 500 with other devices, such as remote control unit 700.

While various embodiments have been described above, it should be understood that they have been presented by way of example only, and not limitation. It will be apparent to persons skilled in the relevant art that various changes in form and detail can be made therein without departing from the spirit and scope of the claimed invention. Thus, the breadth and scope of the claimed invention should not be limited by any of the above-described exemplary embodiments, but should be defined only in accordance with the claims and their equivalents. For example, as one of ordinary skill in the art would appreciate, the present embodiments provide improved or at least alternative wireless communication possibilities compared to prior art devices and wireless communication methods. Active implantable medical devices envisaged by some embodiments include, but are not limited to, cochlear implants, nerve stimulators, pace makers, glucose meters, and any other type of active implantable medical device requiring wireless communication.

U.S. Provisional Patent Application No. 60/924,800, filed on May 31, 2007, and U.S. Provisional Application No. 60/924,807, filed on May 31, 2007, are hereby incorporated by reference in their entirely herein. Similarly, all other patents and publications discussed herein are incorporated in their entirety by reference thereto.

The invention claimed is:

1. A hearing aid, comprising:
a hearing aid component having a housing, wherein the housing is shaped for placement behind and outside an ear of a user, the hearing aid component configured to provide an electrical signal;
an earpiece configured to be arranged in the ear of the user, wherein the earpiece is configured to receive the electrical signal and to provide an acoustic output to the user; and
a coupling element configured for coupling the hearing aid component and the earpiece, the coupling element having an electrically conducting element;
wherein the electrically conducting element in the coupling element of the hearing aid is configured to operate as a part of an antenna for wireless communication, and wherein the electrically conducting element is configured for electromagnetic signal emission and electromagnetic signal reception.

2. The hearing aid of claim 1, wherein the electrically conducting element is configured to transmit the electrical signal from the hearing aid component to the earpiece.

3. The hearing aid of claim 1, further comprising a speaker at the earpiece, wherein the coupling element of the hearing aid comprises two wires coupled to the speaker at the earpiece, and wherein the electrically conducting element comprises at least one of the two wires.

4. The hearing aid of claim 1, wherein the coupling element comprises an additional electrically conducting element for transmitting the electrical signal from the hearing aid component to the earpiece, and wherein the electrically conducting element is a dedicated antenna for the wireless communication.

5. The hearing aid of claim 1, wherein the hearing aid component comprises a wireless communication interface for receiving and/or sending data through the antenna.

6. The hearing aid of claim 1, further comprising a microphone at the hearing aid component.

7. The hearing aid of claim 1, wherein the electrically conducting element comprises one or more conductors configured for wireless communication of data, and for transmission of the electrical signal from the hearing aid component to the earpiece.

8. The hearing aid of claim 1, wherein the electrically conducting element is configured for wireless communication of data and for transmission of the electrical signal in different respective frequency bands.

9. The hearing aid of claim 1, wherein the hearing aid component comprises a wireless communication component and a tuning circuit configured to tune the electrically conducting element in correspondence with the wireless communication component.

10. The hearing aid of claim 1, wherein the coupling element of the hearing aid comprises a connector for connection to the hearing aid component.

11. The hearing aid of claim 1, wherein the earpiece comprises at least a portion sized for insertion into an ear canal of the user.

12. The hearing aid of claim 1, wherein the coupling element of the hearing aid comprises a cable connected between the hearing aid component and the earpiece.

13. A hearing aid, comprising:
a unit having a housing, wherein the housing has a side profile for accommodating at least a rear part of an ear of a user, the unit having a microphone, wherein the unit is configured to provide an electrical signal;
an earpiece configured to be arranged in the ear of the user, wherein the earpiece is configured to receive the electrical signal and to provide an acoustic output to the user, wherein the unit and the earpiece are in an ipsilateral arrangement; and
a coupling element configured for coupling the unit and the earpiece, the coupling element having an electrically conducting element;
wherein the electrically conducting element in the coupling element of the hearing aid is configured to operate as a part of an antenna for wireless communication, and wherein the electrically conducting element is configured for electromagnetic signal emission and electromagnetic signal reception.

14. The hearing aid of claim 13, wherein the electrically conducting element is configured to transmit the electrical signal from the unit to the earpiece.

15. The hearing aid of claim 13, further comprising a speaker at the earpiece, wherein the coupling element of the hearing aid comprises two wires coupled to the speaker at the earpiece, and wherein the electrically conducting element comprises at least one of the two wires.

16. The hearing aid of claim 13, wherein the coupling element comprises an additional electrically conducting element for transmitting the electrical signal from the unit to the earpiece, and wherein the electrically conducting element is a dedicated antenna for the wireless communication.

17. The hearing aid of claim 13, wherein the electrically conducting element comprises one or more conductors configured for wireless communication of data, and for transmission of the electrical signal from the unit to the earpiece.

18. The hearing aid of claim 13, wherein the unit comprises a wireless communication component and a tuning circuit configured to tune the electrically conducting element in correspondence with the wireless communication component.

19. The hearing aid of claim 13, further comprising a user control for facilitating interaction of the user with the hearing aid.

* * * * *